US006645158B2

(12) United States Patent
Mault

(10) Patent No.: US 6,645,158 B2
(45) Date of Patent: Nov. 11, 2003

(54) METABOLIC CALORIMETER EMPLOYING RESPIRATORY GAS ANALYSIS

(75) Inventor: James R. Mault, Evergreen, CO (US)

(73) Assignee: Healthetech, Inc., Golden, CO (US)

( * ) Notice: Subject to any disclaimer, the term of this patent is extended or adjusted under 35 U.S.C. 154(b) by 0 days.

(21) Appl. No.: 10/128,105

(22) Filed: Apr. 23, 2002

(65) Prior Publication Data

US 2002/0183641 A1 Dec. 5, 2002

Related U.S. Application Data

(63) Continuation of application No. 09/601,589, filed as application No. PCT/US99/02448 on Feb. 5, 1999, now Pat. No. 6,402,698.
(60) Provisional application No. 60/104,983, filed on Oct. 20, 1998, and provisional application No. 60/073,812, filed on Feb. 5, 1998.

(51) Int. Cl.[7] ................................................. A61B 5/08
(52) U.S. Cl. ......................... 600/532; 600/538; 600/531
(58) Field of Search ................................. 600/529, 531, 600/532, 533, 538; 73/23.3; 128/204.22, 204.23

(56) References Cited

U.S. PATENT DOCUMENTS

| 2,630,798 A | 3/1953 | White et al. |
| 2,826,912 A | 3/1958 | Kritz |

(List continued on next page.)

FOREIGN PATENT DOCUMENTS

| DE | 198 10 476 | 9/1998 |
| EP | 0 459 647 A2 | 12/1991 |
| GB | 2323292 | 9/1998 |
| WO | 0 712 638 A1 | 12/1995 |
| WO | 96/40340 | 12/1996 |

OTHER PUBLICATIONS

Medical Progress Through Technology, vol 9, No. 1, 1982 Berlin (D), pp. 27–32, R. Salminen et. al., "Computerized Breath–by–Breath Analysis of Respiratory Variables During Exercise."
British Journal of Anaesthesia, vol. 49, 1977 London (GB) pp. 575–587, J.A. Bushman et al., "Closed Circuit Anaesthesia."

(List continued on next page.)

Primary Examiner—Max F. Hindenburg
Assistant Examiner—Navin Natnithithadha
(74) Attorney, Agent, or Firm—Gifford, Krass, Groh, Sprinkle, Anderson & Citkowski, P.C.

(57) ABSTRACT

An indirect calorimeter for measuring the metabolic activity of a subject includes a respiratory connector operative to be supported in contact with the subject so as to pass inhaled and exhaled gases therethrough as the subject breathes, and a flow tube forming a flow pathway for passing inhaled and exhaled gases therethrough, wherein one end of the flow tube is operatively connected to the respiratory connector and the other end of the flow tube is open, and a wall of the flow tube includes an opening. The indirect calorimeter also includes a flow meter adapted to generate a signal as a function of the instantaneous volume of inhaled and exhaled gases in the flow pathway that is in fluid communication with the flow pathway via the opening in the flow tube, and an oxygen sensor operative to generate a signal as a function of the instantaneous fraction of oxygen in the inhaled and exhaled gases in the flow pathway that is in fluid communication with the flow pathway via the opening in the flow tube. The indirect calorimeter further includes a processor for receiving the signals from the flow sensor and the oxygen sensor and using the signals to determine the oxygen consumption of the subject over a period of time.

47 Claims, 2 Drawing Sheets

U.S. PATENT DOCUMENTS

| | | |
|---|---|---|
| 2,831,348 A | 4/1958 | Kritz |
| 2,838,399 A | 6/1958 | Vogel, Jr. |
| 2,869,357 A | 1/1959 | Kritz |
| 2,911,825 A | 11/1959 | Kritz |
| 2,920,012 A | 1/1960 | Sanders et al. |
| 3,212,684 A | 10/1965 | Svensson et al. |
| 3,220,255 A | 11/1965 | Scranton et al. |
| 3,250,270 A | 5/1966 | Bloom |
| 3,306,283 A | 2/1967 | Arp |
| 3,523,529 A | 8/1970 | Kissen |
| 3,527,205 A | 9/1970 | Jones |
| 3,681,197 A | 8/1972 | Smith |
| 3,726,270 A | 4/1973 | Griffis et al. |
| 3,799,149 A | 3/1974 | Rummel et al. |
| 3,814,091 A | 6/1974 | Henkin |
| 3,834,375 A | 9/1974 | Sanctuary et al. |
| 3,895,630 A | 7/1975 | Bachman |
| 3,938,551 A | 2/1976 | Henkin |
| 3,962,917 A | 6/1976 | Terada |
| 3,979,480 A | 9/1976 | Radici et al. |
| 4,003,396 A | 1/1977 | Fleischmann |
| 4,051,847 A | 10/1977 | Henkin |
| 4,078,554 A | 3/1978 | Le Maitre et al. |
| 4,186,735 A | 2/1980 | Henneman et al. |
| 4,188,946 A | 2/1980 | Watson et al. |
| 4,197,857 A | 4/1980 | Osborn |
| 4,200,094 A | 4/1980 | Gedeon et al. |
| 4,211,239 A | 7/1980 | Raemer et al. |
| 4,221,224 A | 9/1980 | Clark |
| 4,230,108 A | 10/1980 | Young |
| 4,341,867 A | 7/1982 | Johansen |
| 4,359,057 A | 11/1982 | Manzella |
| 4,368,740 A | 1/1983 | Binder |
| 4,386,604 A | 6/1983 | Hershey |
| 4,425,805 A | 1/1984 | Ogura et al. |
| 4,440,177 A | 4/1984 | Anderson et al. |
| 4,444,201 A | 4/1984 | Itoh |
| 4,463,764 A | 8/1984 | Anderson et al. |
| 4,572,208 A | 2/1986 | Cutler et al. |
| 4,598,700 A | 7/1986 | Tamm |
| 4,608,995 A | 9/1986 | Linnarsson et al. |
| 4,619,269 A | 10/1986 | Cutler et al. |
| 4,648,396 A | 3/1987 | Raemer |
| 4,658,832 A | 4/1987 | Brugnoli |
| 4,753,245 A | 6/1988 | Gedeon |
| 4,756,670 A | 7/1988 | Arai |
| 4,781,184 A | 11/1988 | Fife |
| 4,796,639 A | 1/1989 | Snow et al. |
| 4,850,371 A | 7/1989 | Broadhurst et al. |
| 4,856,531 A | 8/1989 | Merilainen |
| 4,909,259 A | 3/1990 | Tehrani |
| 4,914,959 A | 4/1990 | Mylvaganam et al. |
| 4,917,108 A | 4/1990 | Mault |
| 4,955,946 A | 9/1990 | Mount et al. |
| 4,986,268 A | 1/1991 | Tehrani |
| 4,998,018 A | 3/1991 | Kurahashi et al. |
| 5,022,406 A | 6/1991 | Tomlinson |
| 5,038,773 A | 8/1991 | Norlien et al. |
| 5,038,792 A | 8/1991 | Mault |
| 5,040,541 A | 8/1991 | Poppendiek |
| 5,042,500 A | 8/1991 | Norlien et al. |
| 5,042,501 A | 8/1991 | Kenny et al. |
| 5,060,506 A | 10/1991 | Douglas |
| 5,060,655 A | 10/1991 | Rudolph |
| 5,060,656 A | 10/1991 | Howard |
| 5,069,220 A | 12/1991 | Casparie et al. |
| 5,072,737 A | 12/1991 | Goulding |
| 5,081,871 A | 1/1992 | Glaser |
| 5,095,900 A | 3/1992 | Fertig et al. |
| 5,095,913 A | 3/1992 | Yelderman et al. |
| 5,117,674 A | 6/1992 | Howard |
| 5,119,825 A | 6/1992 | Huhn |
| 5,178,155 A | 1/1993 | Mault |
| 5,179,958 A | 1/1993 | Mault |
| 5,214,966 A | 6/1993 | Delsing |
| 5,233,996 A | 8/1993 | Coleman et al. |
| 5,282,473 A | 2/1994 | Braig et al. |
| 5,285,794 A | 2/1994 | Lynch |
| 5,293,875 A | 3/1994 | Stone |
| 5,299,579 A | 4/1994 | Gedeon et al. |
| 5,303,712 A | 4/1994 | Van Duren |
| 5,309,921 A | 5/1994 | Kisner et al. |
| 5,326,973 A | 7/1994 | Eckerbom et al. |
| 5,355,879 A | 10/1994 | Brain |
| 5,357,972 A | 10/1994 | Norlien |
| 5,363,857 A | 11/1994 | Howard |
| 5,398,695 A | 3/1995 | Anderson et al. |
| 5,402,796 A | 4/1995 | Packer et al. |
| 5,419,326 A | 5/1995 | Harnoncourt |
| 5,425,374 A | 6/1995 | Ueda et al. |
| 5,450,193 A | 9/1995 | Carlsen et al. |
| 5,468,961 A | 11/1995 | Gradon et al. |
| 5,503,151 A | 4/1996 | Harnoncourt et al. |
| 5,570,697 A | 11/1996 | Walker et al. |
| 5,632,281 A | 5/1997 | Rayburn |
| 5,645,071 A | 7/1997 | Harnoncourt et al. |
| 5,647,370 A | 7/1997 | Harnoncourt |
| 5,676,132 A | 10/1997 | Tillotson et al. |
| 5,705,735 A | 1/1998 | Acorn |
| 5,754,288 A | 5/1998 | Yamamoto et al. |
| 5,789,660 A | 8/1998 | Kofoed et al. |
| 5,796,009 A | 8/1998 | Delsing |
| 5,800,360 A | 9/1998 | Kisner et al. |
| 5,816,246 A | 10/1998 | Mirza |
| 5,831,175 A | 11/1998 | Fletcher-Haynes |
| 5,834,626 A | 11/1998 | De Castro et al. |
| 5,836,300 A | 11/1998 | Mault |
| 5,922,610 A | 7/1999 | Alving et al. |
| 5,932,812 A | 8/1999 | Delsing |
| 5,957,858 A | 9/1999 | Micheels et al. |
| 6,010,459 A | 1/2000 | Silkoff et al. |
| 6,044,843 A | 4/2000 | O'Neill et al. |

OTHER PUBLICATIONS

IEEE Transactions on Biomedical Engineering, vol. 35, No. 9 Sep. 1998, pp. 653–659, Capek et. al., "Noninvasive Measurement of Cardiac Output Using Partial CO2 ReBreathing."

Clinics in Chest Medicine (Review), vol. 10, 1989, pp. 255–264, Heigenhauser et. al., "Measurement of Cardiac Output by Carbon Dioxide Rebreathing Methods."

Determination of Nitric Oxide Levels by Fluorescence Spectroscopy, Gabor G. and Allon N. in Biochemical Pharmacological and Clinical Aspects of Nitric Oxide, edited by B.A. Weissman et. al., Plenum Press, New York, 1995, p. 57.

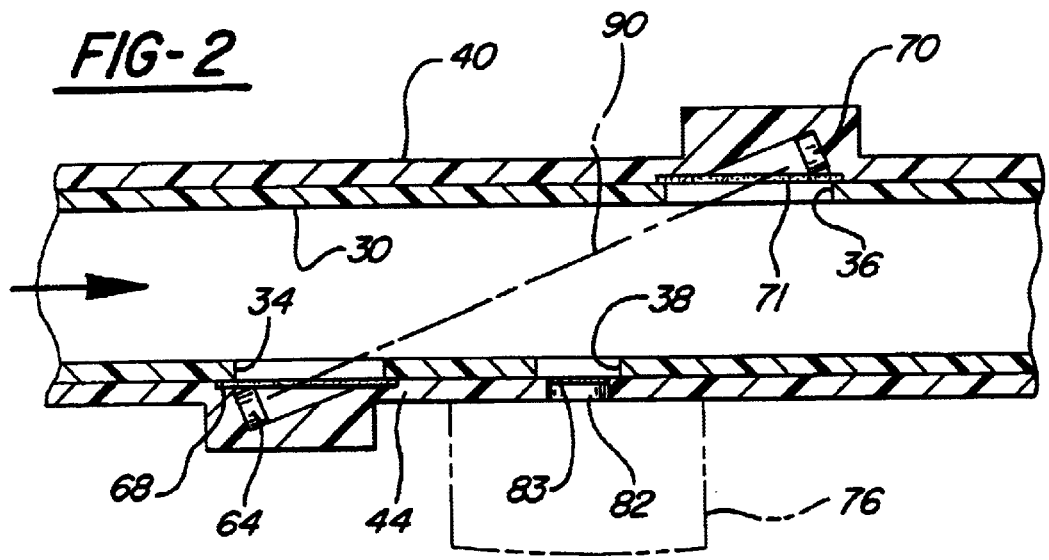
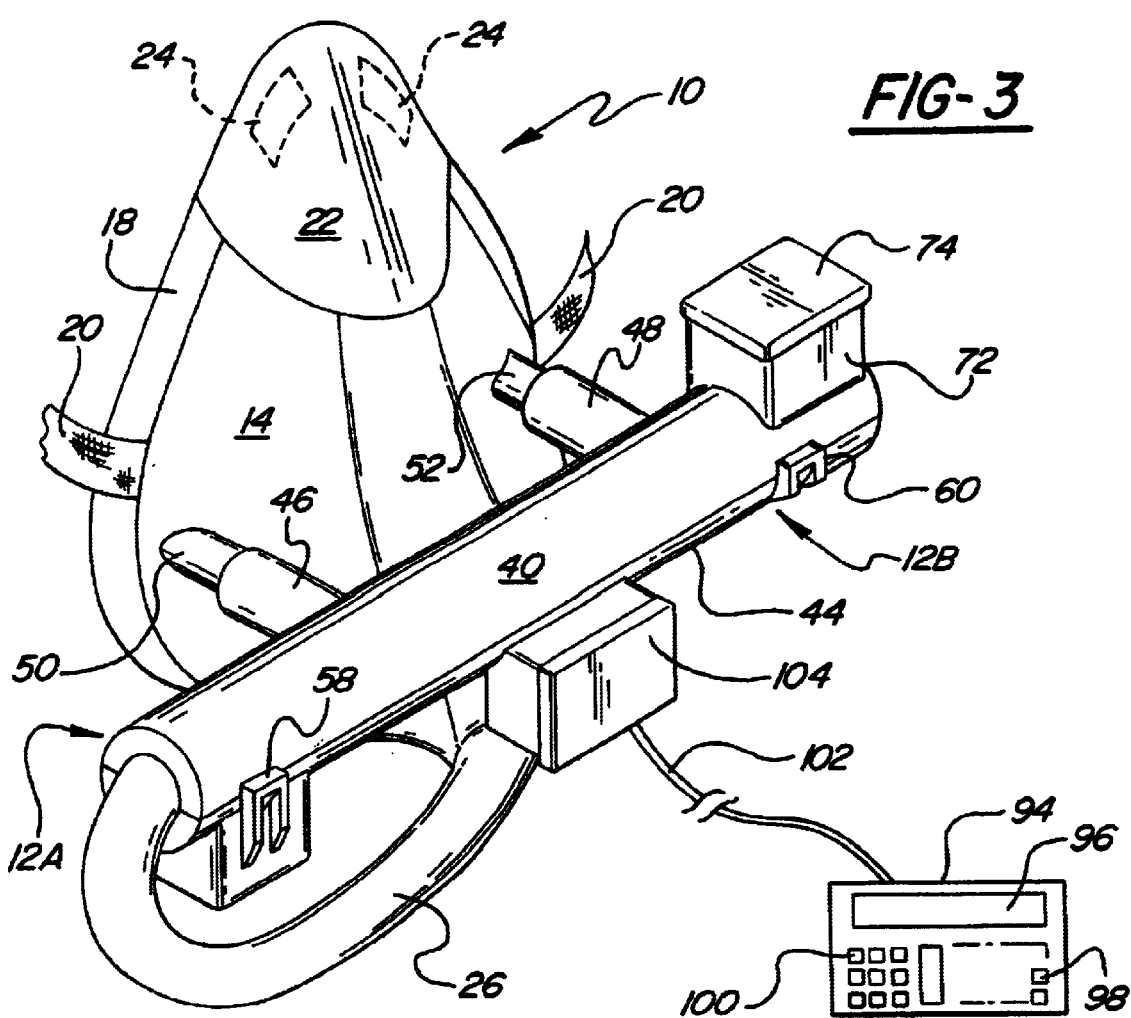

METABOLIC CALORIMETER EMPLOYING RESPIRATORY GAS ANALYSIS

RELATED APPLICATIONS

This application is a continuation of U.S. patent application Ser. No. 09/601,589 filed Sep. 19, 2000, now U.S. Pat. No. 6,402,698 B1 issued Jun. 11, 2002, which is a 371 of international PCT/US99/02448 filed Feb. 5, 1999, which claims priority of U.S. Provisional Application Serial No. 60/073,812, filed Feb. 5, 1998; and No. 60/104,983, filed Oct. 20, 1998.

FIELD OF THE INVENTION

This invention relates to a respiratory instrument for measuring metabolism and in particular to a metabolic calorimeter for relating respiratory parameters by indirect calorimetry.

BACKGROUND OF THE INVENTION

U.S. Pat. Nos. 5,038,792; 5,178,155; 5,179,958; and 5,836,300, all to the same inventor as the present application, disclose systems for measuring metabolism and related respiratory parameters through indirect calorimetry. These instruments employ bi-directional flow meters which pass both the inhalations and the exhalations of a user breathing through the instrument and integrate the resulting instantaneous flow signals to determine total full flow volumes. The concentration of carbon dioxide generated by the user is determined by either passing the exhaled volume through a carbon dioxide scrubber before it passes through the flow meter, so that the differences between the inhaled and exhaled volumes is essentially a measurement of the carbon dioxide contributed by the lungs, or by the measurement of the instantaneous carbon dioxide content of the exhaled volume with a capnometer and integrating that signal with the exhaled flow volume. The oxygen consumption can then be calculated.

The scrubber used with certain of these systems was relatively bulky and required replenishment after extended usage. The capnometers used with the instruments to measure carbon dioxide concentration had to be highly precise and accordingly expensive because any error in measurement of the carbon dioxide content of the exhalation produces a substantially higher error in the resulting determination of the oxygen contents of the exhalation. Thus, there is a need in the art for an indirect calorimeter for measuring the metabolic activity and related respiratory parameters of a user.

SUMMARY OF THE INVENTION

The present invention is an indirect calorimeter for measuring the metabolic activity of a subject. The indirect calorimeter includes a respiratory connector operative to be supported in contact with the subject so as to pass inhaled and exhaled gases therethrough as the subject breathes, and a flow tube forming a flow pathway for passing inhaled and exhaled gases therethrough, wherein one end of the flow tube is operatively connected to the respiratory connector and the other end of the flow tube is open, and a wall of the flow tube includes an opening. The indirect calorimeter also includes a flow meter adapted to generate a signal as a function of the instantaneous volume of inhaled and exhaled gases in the flow pathway that is in fluid communication with the flow pathway via the opening in the flow tube, and an oxygen sensor operative to generate a signal as a function of the instantaneous fraction of oxygen in the inhaled and exhaled gases in the flow pathway that is in fluid communication with the flow pathway via the opening in the flow tube. The indirect calorimeter further includes a processor for receiving the signals from the flow senor and the oxygen sensor and using the signals to determine the oxygen consumption of the subject over a period of time.

The present invention overcomes the disadvantages associated with prior art indirect calorimeters by providing a respiratory calorimeter in which both the inhaled and exhaled flow volumes pass through a flow meter which provides an output representative of the instantaneous flow rate and the inhalations and exhalations also pass over an oxygen sensor providing an output as a function of the instantaneous oxygen concentration in the flowing gas. These two signals are provided to a computer which integrates them to derive signals representative of the inhaled and exhaled oxygen volume. From these measurements the oxygen consumption, respiratory quotient and related respiratory parameters are calculated and displayed.

One advantage of the present invention is that the indirect calorimeter utilizes an ultrasonic transit time flow meter and a fluorescence quench oxygen sensor. Both of these sensors operate upon the respiratory gasses as they pass through a flow tube with a substantially continuous, uninterrupted internal diameter so that the flow is substantially laminar. Previous indirect calorimeters, including those disclosed in the above-described U.S. patents, have employed flow measurement techniques that require protrusions in the flow path such as pressure differential transducers, hot wire transducers or the like. Great difficulties are encountered in maintaining a largely laminar flow in transducers of this type, resulting in inaccuracies in the flow measurement. The present invention preferably employs a volume flow meter which transmits ultrasonic pulses through the flow stream in a direction either parallel to the flow path or at least having a component parallel to the flow path. The transit time of the pulses is a function of the flow rate of the gas and because the interior diameter of the flow tube wall is substantially uninterrupted, laminar flow conditions are maintained providing a high uniformity of measurement.

Another advantage of the present invention is that an indirect calorimeter is provided that directly measures the oxygen concentration in the inhaled and exhaled gasses passing through the flow tube by a technique which does not introduce any protuberances into the flow area and which may be positioned to measure the oxygen content in the same area in which flow is measured. Thus, unlike previous systems which require some linear separation between the point of flow measurement and the point of gas analysis, and accordingly would result in inaccuracies were the two to be integrated, the present system does not create any phase lag between the oxygen measurement and the flow measurement which would otherwise result in inaccuracies and the need for signal processing to correct for the displacement of the measurements. The preferred embodiment of the invention employs a fluorescence quench technique for oxygen measurement which utilizes a fluoresceable chemical disposed on the interior diameter of the flow wall in the area of ultrasonic pulse transmission. This fluorescent coating may be formed on the tube wall directly or supported on the end of a fiber optic probe terminating in alignment with the interior diameter of the tube. This coating is subjected to exciting radiation from the exterior of the tube and the resulting fluorescence may be measured from the exterior. The fluorescence is quenched by oxygen passing over the coating and the percentage of oxygen in the flow tube can be instantaneously measured by the intensity of the fluorescence.

Still another advantage of the present invention is that the flow tube is preferably formed as a disposable insert which may be inserted into a permanent, reusable structure which includes the ultrasonic transmitter and receiver and the fluorescence oxygen sensor. The fluorescent coating may be covered on the tube side with a microbial filter formed as part of the disposable insert. This filter prevents the fluorescent coating from being bacterially contaminated. The disposable insert is utilized to avoid the spread of disease from user to user in situations in which the indirect calorimeter is used by a succession of persons. The insert is preferably produced of an inexpensive material such as plastic.

A further advantage of the present invention is that the disposable insert is supported by a disposable breathing mask that covers the nose and the mouth of the user, allowing normal breathing over the measurement time. Most prior art devices have employed mouthpieces; however, it has been determined that in many users the mouthpiece can induce a mild form of hyperventilation which increases the user's energy consumption and results in erroneous metabolic readings. In one embodiment of the present invention, the metabolic measurement components are integrated with and are contained within the mask with no requirement for external connections. When the mask is attached to the user's head by straps, adhesive, or the like, it allows a full range of user movement during the measurement. Thus, it can be used during normal exercise to allow determination of the effect of that activity on respiratory parameters and may also be used to measure resting energy expenditure. The increased user comfort resulting from the elimination of connections between the mask and associated apparatus allows measurements to be made over longer periods of time and minimizes the labored breathing often associated with conventional respiratory masks which affects accurate measurement of energy expenditure.

Still a further advantage of the present invention is that the mask preferably incorporates a nasal spreader on its interior surface which adhesively attaches to the nares of the user's nose and pulls them outwardly to enlarge the nose flow area and minimize the energy expenditure in breathing, which is often increased with conventional masks.

Yet still a further advantage of the present invention is that the computation unit and display and controls are supported in a separate desktop unit and connected to the sensors within the mask by highly flexible cables.

Other features and advantages of the present invention will be readily appreciated, as the same becomes better understood after reading the subsequent description taken in conjunction with the accompanying drawings.

BRIEF DESCRIPTION OF THE DRAWINGS

FIG. 2 is a cross-sectional view through the flow tube of FIG. 1; and

FIG. 3 is a perspective view of a second embodiment employing a desktop computation and display unit.

DETAILED DESCRIPTION OF THE INVENTION

Figure 1:
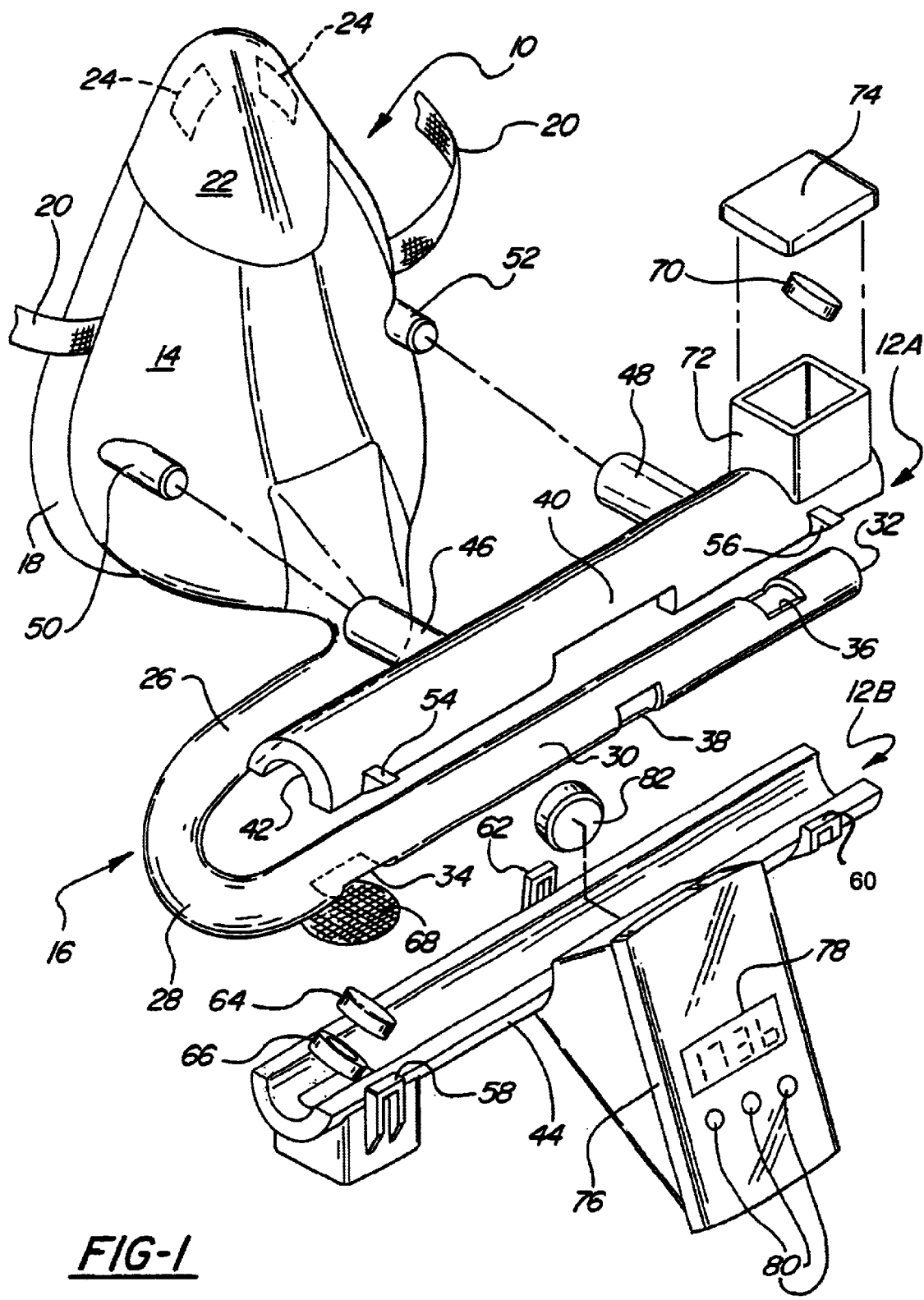
FIG. 1 is a perspective view in exploded form of a first embodiment of the invention.

Referring to FIGS. 1 and 2, a preferred embodiment of the invention includes a disposable section, generally indicated at 10, and a nondisposable section shown exploded into parts generally indicated at 12a and 12b. The disposable section 10 is made of low cost materials and is intended to be replaced when the calorimeter is employed by serial users to avoid hygiene problems such as transfer of bacterial infections. The disposable section 10 may be retained by a user for reuse at a later date or may be discarded. If the calorimeter is repeatedly used by a single user, the section 10 need not be discarded between uses. The section 10 broadly consists of a mask 14 and a U-shaped breathing tube generally indicated at 16. The mask is adapted to be retained over a user's face so as to cover the user's nose and mouth. The mask 14 has a resilient edge section 18 which engages the user's face in an airtight manner. The mask may be supported against the user's face by the user holding the outer side, but preferably the mask has straps 20 which connect to its edges and pass around the rear of the user's head. Alternatively, the mask could be retained by a pressure sensitive coating formed on the edge seal 18.

The mask proper is preferably formed of a rigid plastic but the section 22 at the top of the mask which is intended to surround the user's nose, is preferably formed of a more resilient material. Pressure sensitive adhesive pads 24 are formed on the interior surfaces of the nose section 22 and allow the user to press the outer surfaces of the nose section together so as to engage the outer surfaces of the user's nares with the pressure sensitive pads 24. When the pressure on the outer surface of the nose section 22 is released, the sections will spring outwardly and will pull the nares away from the nose so as to enable easy breathing through the nose into the mask.

The U-shaped breathing tube 16 connects to the interior of the mask 14. The tube then extends from the lower forward section of the mask and extends laterally as at 26 to the right of the user in a generally horizontal plane. At the extreme right it forms a 180 degree bight 28 and extends to the left of the user in an elongated measurement section 30. The far end of the tube 16 is opened at 32 so that as the user inhales while wearing the mask 14 air is drawn into the tube 16 through the end 32 and as the user exhales air is expelled through the end 32. The straight section 30 of the tube has three windows or openings, one, 34, formed at its lower side adjacent to the bight 28, the second, 36, formed on its upper side adjacent to the opening 32 and a third, 38, formed on the side of the tube in the middle of the section 30.

The nondisposable portion of the calorimeter consists of the interlocking upper section 12a and lower section 12b. The upper section 12a is formed about a semi-cylindrical section of tube 40. The inner diameter 42 of the tube section 40 matches the outer diameter of the disposable tube section 30 and the section 40 is slightly shorter than the straight line tube section 30. Similarly, the nondisposable section 12b is formed of a semi-cylindrical tube half 44 having an inner diameter matching the outer diameter of the tube section 30 and having a slightly shorter length.

The tube section 40 is formed with two rearward facing tubular supports 46 and 48, spaced along its length. These supports removably engage bosses 50 and 52 which are formed integrally with the face mask 14 and project forwardly from its upper sides. The lower tube section 44 is then locked to the upper tube section 40 so as to surround the breathing tube section 30. Cam sections 54 and 56 formed at the forward end of the tube section 40 engage latches 58 and 60 formed on the lower tube half and a similar cam (not shown) projecting from the rear of the tube 40 engages a latch 62 formed at the rear of the lower tube section 44 adjacent its free edge.

The nondisposable section also includes a flow meter. One example of a flow meter is a bi-directional flow meter.

Another example of a flow meter is an ultrasonic transducer, such as the ultrasonic transceiver shown at 64. Preferably, the ultrasonic transducer is strategically placed to bi-directionally transmit and receive ultrasonic signals. Still another example of an ultrasonic flow meter is manufactured by NDD Medizintechnik AG, of Zurich, Switzerland, and disclosed in U.S. Pat. Nos. 3,738,169; 4,425,805; 5,419,326; and 5,645,071.

In this example, the ultrasonic transceiver 64 is housed in a ring 66 formed in the lower tube section 44, and projects into the window 34 of the tube section 30. An anti-microbial filter 68 covers the surface of the transducer 64. Similarly, an ultrasonic transducer, such as an ultrasonic receiver as shown at 70, is supported within a section 72 formed on the upper tube 40, and protected by a cover 74. The ultrasonic receiver 70 projects into the window 36 adjacent the outlet and inlet end of the tube 30. An anti-microbial filter (not shown) may protect the surface of the transducer. The lower tubing section 44 is integrally formed with a housing 76 which contains the microprocessor which receives the signals from the transducers and sensors and controls their operation, and computes the oxygen consumption and other respiratory factors measured by the device. The unit 76 includes a display 78 and control switches 80. In certain embodiments of the invention a digital keypad may be included on the unit 76.

The computation unit determines oxygen consumption by solving the equation $VO_2=V_I \times (F_IO_2)-V_E \times (FEO_2)$ where $VO_2$ is the consumed oxygen, $V_I$ is the inhaled volume, $V_E$ is the exhaled volume, $F_IO_2$ is the fraction of oxygen in the inhalation, and $FEO_2$ is the fraction of volume in the exhalation. The system integrates the instantaneous flow volumes with the instantaneous oxygen levels over an entire breathing cycle, which is typically four to five minutes. Other respiratory parameters such as RQ, REE, etc. may be calculated in the manner disclosed in my previous issued patents.

An oxygen concentration sensor 82 is supported within the housing 76 so that when the tube sections 40 and 44 are joined, the surface of the oxygen sensor, preferably covered with an anti-microbial filter 83, is disposed within the window 38 so that its outer surface is substantially flush with the internal diameter of the tube section 30.

The oxygen concentration sensor 82 is preferably of the fluorescent quench type as disclosed in U.S. Pat. Nos. 3,725,658; 5,517,313 and 5,632,958. One example of such a sensor is a sensor manufactured by Sensors for Medicine and Science, Inc. of Germantown, Md. The computation unit includes a source (not shown) for directing exciting radiation to the fluorescent coating on the end of the oxygen sensor 82 from exterior of the tube 30 and sensing the resulting fluorescence intensity which is diminished as a function of the concentration of oxygen and gas flowing over its surface to produce a direct measurement of oxygen concentration. The exciting radiation and fluorescent signal may be carried to the sensor by an optical fiber (not shown).

In use, a subject dons the mask 14 and attaches the straps so that the subject's nose is disposed within the section 22 of the mask, the subject's mouth is covered, and the area surrounding the mouth and nose are sealed by contact of the section 18 with the subject's face. The subject then pinches the outer surface of the section 22 of the mask so that the adhesive pads 24 are brought into pressured contact with the two sides of the subject's nose. The resilient section 22 is released so that the nares are separated, allowing free breathing within the mask.

Either prior to donning the mask or subsequently, the nondisposable sections 12a and 12b are attached so as to surround the tube 30 and the connecting sections 46 and 48 are attached to the bosses 50 and 52 on the front surface of the mask 14.

The user may then breathe in a normal manner so that the inhalations and exhalations are passed through the tube 16 and connect to the atmosphere at the tube end 32. After the subject has breathed through the mask for a minute or two to stabilize the breathing, one of the buttons 80 is depressed to start the measuring cycle. In alternative embodiments of the invention, rather than manually depressing the button 80 to start the measuring cycle, the computation unit 76 could sense the flow of gasses through the tube 30 and automatically initiate the measurement cycle when the breathing reached a normal level.

Preferably, the ultrasonic transducers 64 and 70 face each other and transmit and receive ultrasonic pulses along a path 90 illustrated in FIG. 2 or some alternative path which is either parallel to or has a substantial component in the direction of the flow. The gas flow acts to advance or retard the flow of the pulses so that the full transmit time of the pulses is a function of the flow rate.

In practice, after a user's breathing has stabilized and a test cycle is initiated either automatically or through manual depressions of one of the buttons 80, the flow rate and oxygen levels through the tube 30 are monitored by the sensors and provided to the computation unit. At the end of the cycle, which is preferably automatically timed, the measured quantity such as oxygen consumption will be shown on the display 78.

FIG. 3 illustrates an alternative embodiment of the invention in which the computation and display unit, 76, instead of being incorporated integrally with the nondisposable section which is secured to the master in use, is formed in a separate desktop unit 94. The unit incorporates a display 96, control switches 98, and a keyboard 100. It is connected to the section 12a by a flexible electrical cable 102. This arrangement lowers the weight of the unit which must be supported on the mask 14 during testing and allows more convenient user control of the unit and observation of the display. The computation and control unit 76 of the first embodiment is replaced in the embodiment by a box 104 which includes a connector for the cable 102 and also supports the oxygen sensor 82 in the same manner as the embodiment illustrated in FIG. 1. Otherwise, the system of FIG. 3 is identical to the system of FIG. 1 and similar numerals are used for similar sections.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

We claim:

1. An indirect calorimeter for measuring the metabolic activity of a subject comprising:
   a respiratory connector operative to be supported in contact with the subject so as to pass inhaled and exhaled gases therethrough as the subject breathes;
   a flow tube forming a flow pathway for passing inhaled and exhaled gases therethrough as the subject breathes, wherein one end of the flow tube is operatively connected to the respiratory connector and the other end of the flow tube is open, and a wall of the flow tube includes an opening;

a flow meter adapted to generate a signal as a function of the instantaneous volume of inhaled and exhaled gases in the flow pathway, wherein said flow meter is in fluid communication with the flow pathway via the opening in said flow tube;

an oxygen sensor operative to generate a signal as a function of the instantaneous fraction of oxygen in the inhaled and exhaled gases in the flow pathway, wherein said oxygen sensor is in fluid communication with the flow pathway via the opening in said flow tube; and a processor for receiving said signals from said flow sensor and said oxygen sensor and using the signals to determine the oxygen consumption of the subject over a period of time.

2. The indirect calorimeter of claim 1 wherein said oxygen consumption is determined from the integral of the instantaneous flow volume during inhalation, multiplied by the instantaneous oxygen content measured at the time of measuring the instantaneous flow volume, and subtracting from that integral the integral of the instantaneous flow volume during exhalation multiplied by the instantaneous oxygen content measured at the time of measuring the instantaneous flow volume.

3. The indirect calorimeter of claim 1 wherein said flow tube is a U-shaped member having a first end operatively connected to the respiratory connector, an elongated measurement section, and a second end that is open.

4. The indirect calorimeter of claim 1 wherein said respiratory connector is a mask having a free edge which forms a seal about a portion of a subject's face.

5. The indirect calorimeter of claim 1 having a disposable portion operatively connected to a nondisposable portion, wherein said disposable portion includes said respiratory connector and said flow tube, and said nondisposable portion includes said flow meter, oxygen sensor, and processor.

6. The indirect calorimeter of claim 5, wherein said nondisposable portion includes a housing having an integrally formed support member for operatively supporting a measurement section of the flow tube, and the support member includes an interlocking upper section and lower section, with the upper section and lower section each forming a semi-cylindrical tube half.

7. The indirect calorimeter of claim 6, wherein said flow meter is supported on either one of said interlocking upper section or said lower section, so that the flow meter projects into the opening in the flow tube.

8. The indirect calorimeter of claim 7 wherein a microbial filter covers a surface of the flow meter.

9. The indirect calorimeter of claim 1, wherein said flow meter is a bi-directional flow meter.

10. The indirect calorimeter of claim 9, wherein said bi-directional flow meter is an ultrasonic flow meter.

11. The indirect calorimeter of claim 6, wherein said oxygen sensor is supported on either one of said interlocking upper section or said lower section, so that the oxygen sensor projects into the opening in the flow tube.

12. The indirect calorimeter of claim 11, wherein a microbial filter covers a surface of the oxygen sensor.

13. The indirect calorimeter of claim 1, wherein said oxygen sensor is a fluorescence quench oxygen sensor.

14. The indirect calorimeter of claim 1, wherein said processor includes a keyboard and a visual display.

15. The indirect calorimeter of claim 1, having a disposable portion operatively connected to a nondisposable portion that is operatively in communication with a remotely located processor, wherein said respiratory connector forms the disposable portion, and said flow meter and oxygen sensor form the nondisposable portion.

16. The indirect calorimeter of claim 1 wherein the flow of respiratory gas through the flow tube is sensed by said processor, which initiates measurement of respiratory gases when the flow of respiratory gas meets a predetermined measurement criteria.

17. The indirect calorimeter of claim 1, wherein said processor calculates the subject's carbon dioxide production over a period of time in accordance with the following equation:

$$V_{CO2} = [V_E - (V_E \cdot F_E O_2)] - [V_I - (V_I \cdot F_I O_2)].$$

18. An indirect calorimeter for measuring the metabolic activity of a subject comprising:

a disposable portion having a respiratory connector operative to be supported in contact with the subject, so as to pass inhaled and exhaled gases therethrough as the subject breathes, and a flow tube forming a flow pathway for passing inhaled and exhaled gases therethrough, wherein one end of the flow tube is operatively connected to the respiratory connector and the other end of the flow tube is open, and a wall of the flow tube includes an opening; and a nondisposable portion operatively connected to the disposable portion, having a flow meter in fluid communication with the flow pathway via the opening in said flow tube and adapted to generate a signal as a function of the instantaneous volume of inhaled and exhaled gases in the flow pathway, an oxygen sensor in fluid communication with the flow pathway via the opening in said flow tube and operative to generate a signal as a function of the instantaneous fraction of oxygen in the inhaled and exhaled gases in the flow pathway, and a processor for receiving said signals from said flow sensor and said oxygen sensor and using the signals to determine the metabolic activity of the subject.

19. The indirect calorimeter of claim 18 wherein the metabolic activity is oxygen consumption as determined from the integral of the instantaneous flow volume during inhalation, multiplied by the instantaneous oxygen content measured at the time of measuring the instantaneous flow volume, and subtracting from that integral the integral of the instantaneous flow volume during exhalation multiplied by the instantaneous oxygen content measured at the time of measuring the instantaneous flow volume.

20. The indirect calorimeter of claim 18 wherein said flow tube is a U-shaped member having a first end operatively connected to the respiratory connector, an elongated measurement section, and a second end that is open.

21. The indirect calorimeter of claim 18 wherein said respiratory connector is a mask having a free edge which forms a seal about a portion of a subject's face.

22. The indirect calorimeter of claim 18, wherein said nondisposable portion includes a housing having an integrally formed support member for operatively supporting a measurement section of the flow tube, and the support member includes an interlocking upper section and lower section, with the upper section and lower section each forming a semi-cylindrical tube half.

23. The indirect calorimeter of claim 22, wherein said flow meter is supported on either one of said interlocking upper section or said lower section, so that the flow meter projects into the opening in the flow tube.

24. The indirect calorimeter of claim 23 wherein a microbial filter covers a surface of the flow meter.

25. The indirect calorimeter of claim 22, wherein said flow meter is a bi-directional flow meter.

26. The indirect calorimeter of claim 25, wherein said bi-directional flow meter is an ultrasonic flow meter.

27. The indirect calorimeter of claim 22, wherein said oxygen sensor is supported on either one of said interlocking upper section or said lower section, so that the oxygen sensor projects into the opening in the flow tube.

28. The indirect calorimeter of claim 27 wherein a microbial filter covers a surface of the oxygen sensor.

29. The indirect calorimeter of claim 18, wherein said oxygen sensor is a fluorescence quench oxygen sensor.

30. The indirect calorimeter of claim 18, wherein said processor includes a keyboard and a visual display.

31. The indirect calorimeter of claim 18 wherein the flow of respiratory gas through the flow tube is sensed by said processor, which initiates measurement of respiratory gases when the flow of respiratory gas meets a predetermined measurement criteria.

32. The indirect calorimeter of claim 18, wherein said processor calculates the subject's carbon dioxide production over a period of time in accordance with the following equation:

$$V_{CO2} = [V_E - (V_E \cdot F_E O_2)] - [V_I - (V_I \cdot F_I O_2)].$$

33. An indirect calorimeter for measuring the metabolic activity of a subject comprising:
  a disposable portion having a respiratory connector operative to be supported in contact with the subject, so as to pass inhaled and exhaled gases therethrough as the subject breathes, and a flow tube forming a flow pathway for passing inhaled and exhaled gases therethrough, wherein one end of the flow tube is operatively connected to the respiratory connector and the other end of the flow tube is open, and a wall of the flow tube includes an opening;
  a nondisposable portion operatively connected to the disposable portion, having a flow meter in fluid communication with the flow pathway via the opening in said flow tube and adapted to generate a signal as a function of the instantaneous volume of inhaled and exhaled gases in the flow pathway, an oxygen sensor in fluid communication with the flow pathway via the opening in said flow tube and operative to generate a signal as a function of the instantaneous fraction of oxygen in the inhaled and exhaled gases in the flow pathway; and
  a processor for receiving said signals from said flow sensor and said oxygen sensor and using the signals to determine the metabolic activity of the subject.

34. The indirect calorimeter of claim 33 wherein the metabolic activity is oxygen consumption as determined from the integral of the instantaneous flow volume during inhalation, multiplied by the instantaneous oxygen content measured at the time of measuring the instantaneous flow volume, and subtracting from that integral the integral of the instantaneous flow volume during exhalation multiplied by the instantaneous oxygen content measured at the time of measuring the instantaneous flow volume.

35. The indirect calorimeter of claim 33 wherein said flow tube is a U-shaped member having a first end operatively connected to the respiratory connector, an elongated measurement section, and a second end that is open.

36. The indirect calorimeter of claim 33 wherein said respiratory connector is a mask having a free edge which forms a seal about a portion of a subject's face.

37. The indirect calorimeter of claim 33, wherein said nondisposable portion includes a housing having an integrally formed support member for operatively supporting the measurement section of the flow tube, and the support member includes an interlocking upper section and lower section, with the upper section and lower section each forming a semi-cylindrical tube half.

38. The indirect calorimeter of claim 37, wherein said flow meter is supported on either one of said interlocking upper section or said lower section, so that the flow meter projects into the opening in the flow tube.

39. The indirect calorimeter of claim 38 wherein a microbial filter covers a surface of the flow meter.

40. The indirect calorimeter of claim 33, wherein said flow meter is a bi-directional flow meter.

41. The indirect calorimeter of claim 40, wherein said bi-directional flow meter is an ultrasonic flow meter.

42. The indirect calorimeter of claim 37, wherein said oxygen sensor is supported on either one of said interlocking upper section or said lower section, so that the oxygen sensor projects into the opening in the flow tube.

43. The indirect calorimeter of claim 42 wherein a microbial filter covers a surface of the oxygen sensor.

44. The indirect calorimeter of claim 33 wherein said oxygen sensor is a fluorescence quench oxygen sensor.

45. The indirect calorimeter of claim 33, wherein said processor includes a keyboard and a visual display.

46. The indirect calorimeter of claim 33 wherein the flow of respiratory gas through the flow tube is sensed by said processor, which initiates measurement of respiratory gases when the flow of respiratory gas meets a predetermined measurement criteria.

47. The indirect calorimeter of claim 33, wherein said processor calculates the subject's carbon dioxide production over a period of time in accordance with the following equation:

$$V_{CO2} = [V_E - (V_E \cdot F_E O_2)]$$
$$- [V_I - (V_I \cdot F_I O_2)].$$

* * * * *